United States Patent
Sim et al.

(10) Patent No.: US 10,947,495 B2
(45) Date of Patent: Mar. 16, 2021

(54) **MICROORGANISM OF THE GENUS *ESCHERICHIA* PRODUCING O-PHOSPHOSERINE AND A METHOD FOR PRODUCING O-PHOSPHOSERINE OR L-CYSTEINE USING THE SAME**

(71) Applicant: CJ Cheiljedang Corporation, Seoul (KR)

(72) Inventors: Se Hoon Sim, Seoul (KR); Seo-Yun Kim, Suwon-si (KR); Sol Kim, Suwon-si (KR); Hye Won Kim, Seongnam-si (KR); Inhwa Yoo, Yongin-si (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 16/474,291

(22) PCT Filed: Dec. 28, 2017

(86) PCT No.: PCT/KR2017/015663
§ 371 (c)(1),
(2) Date: Jun. 27, 2019

(87) PCT Pub. No.: WO2018/124778
PCT Pub. Date: Jul. 5, 2018

(65) Prior Publication Data
US 2019/0338242 A1 Nov. 7, 2019

(30) Foreign Application Priority Data
Dec. 29, 2016 (KR) .......................... 10-2016-0182947

(51) Int. Cl.
*C12N 1/20* (2006.01)
*C12P 13/06* (2006.01)
*C12P 13/12* (2006.01)
*C12R 1/19* (2006.01)

(52) U.S. Cl.
CPC ................ *C12N 1/20* (2013.01); *C12P 13/06* (2013.01); *C12P 13/12* (2013.01); *C12R 1/19* (2013.01); *C12Y 205/01065* (2013.01)

(58) Field of Classification Search
CPC ......... C12N 1/20; C12N 9/1085; C12P 13/06; C12P 13/12; C12R 1/19; C12Y 205/01065
See application file for complete search history.

(56) References Cited

U.S. PATENT DOCUMENTS

| | | |
|---|---|---|
| 2012/0190081 A1 | 7/2012 | Chang et al. |
| 2014/0335561 A1 | 11/2014 | Park et al. |
| 2015/0004657 A1 | 1/2015 | Song et al. |
| 2016/0115507 A1 | 4/2016 | Kim et al. |
| 2017/0260556 A1 | 9/2017 | Kim et al. |

FOREIGN PATENT DOCUMENTS

| | | |
|---|---|---|
| EP | 0885962 B1 | 4/2005 |
| KR | 10-2012-0041115 A | 4/2012 |
| KR | 10-1404376 B1 | 6/2014 |
| KR | 10-2014-0133744 A | 11/2014 |
| KR | 10-2014-0133754 A | 11/2014 |
| KR | 10-2016-0020050 A | 2/2016 |

OTHER PUBLICATIONS

International Search Report dated Apr. 16, 2018 for International Patent Application No. PCT/KR2017/015663, Sim et al., "*Escherichia* sp. microorganism producing o-phosphoserine and method for producing o-phosphoserine or l-cysteine using same," filed Dec. 28, 2017 (7 pages).
Peters-Wendisch et al., "Metabolic engineering of Corynebacterium glutamicum for L-serine production," Appl Environ Microbiol. 71(11):7139-44 (2005).
Ryu et al., "Continuous L-cysteine production using immobilized cell reactors and product extractors," Process Biochemistry. 32(3):201-9 (1997).
Wada et al., "Metabolic pathways and biotechnological production of L-cysteine," Appl Microbiol Biotechnol. 73(1):48-54 (2006).
Wendisch et al., "Metabolic engineering of *Escherichia coli* and Corynebacterium glutamicum for biotechnological production of organic acids and amino acids," Curr Opin Microbiol. 9(3):268-74 (2006).
Zahoor et al., "Metabolic engineering of Corynebacterium glutamicum aimed at alternative carbon sources and new products," Comput Struct Biotechnol J. 3:e201210004 (2012) (11 pages).

*Primary Examiner* — Padmavathi Baskar
(74) *Attorney, Agent, or Firm* — Clark & Elbing LLP; Susan M. Michaud

(57) ABSTRACT

The present application relates to a microorganism producing O-phosphoserine and a method for producing O-phosphoserine, cysteine or a cysteine derivative using same.

4 Claims, No Drawings

MICROORGANISM OF THE GENUS *ESCHERICHIA* PRODUCING O-PHOSPHOSERINE AND A METHOD FOR PRODUCING O-PHOSPHOSERINE OR L-CYSTEINE USING THE SAME

TECHNICAL FIELD

The present disclosure relates to a microorganism producing O-phosphoserine and a method for producing O-phosphoserine, cysteine, or cysteine derivatives using the same.

BACKGROUND ART

As an important amino acid in sulfur metabolism in all organisms, L-cysteine is used not only in the synthesis of in vivo proteins such as the keratin of hair, etc., glutathione, biotin, methionine, and other sulfur-containing metabolites, but also as a precursor in coenzyme biosynthesis.

With regard to a method for producing L-cysteine using a microorganism, 1) a method for biologically converting D,L-2-aminothiazoline-4-carboxylic acid (D,L-ATC) using a microorganism (Ryu OH et al., Process Biochem., 32:201-209, 1997) and 2) a method for producing L-cysteine by direct fermentation using *Escherichia coli* are known (European Patent No. EP0885962B; Wada M and Takagi H, Appl. Microbiol. Biochem., 73:48-54, 2006). Additionally, 3) a method for producing O-phosphoserine (hereinafter referred to as "OPS") by fermentation using a microorganism followed by converting O-phosphoserine into L-cysteine by reacting with a sulfide under the catalysis of O-phosphoserine sulfhydrylase (hereinafter referred to as "OPSS") is known in the art (Korean Patent No. 10-1381048).

In particular, it is necessary to produce OPS, a precursor, in order to produce cysteine by the above method 3). For example, OPS can be produced through the adjustment of activities of SerA, SerC, and SerB, enzymes in the L-serine biosynthesis pathway in microorganisms (Ahmed Zahoor, Computational and structural biotechnology journal, Vol 3.2012 October; Wendisch VF et al., Curr Opin Microbiol. 2006 June, 9(3):268-74; PetersWendisch P et al., Appl Environ Microbiol. 2005 November, 71(11):7139-44.).

DISCLOSURE

Technical Problem

As a result of intensive efforts to develop an OPS-producing microorganism, the present inventors developed a microorganism capable of producing OPS with high yield by further improving resistance to OPS, thereby completing the present disclosure.

Technical Solution

An object of the present disclosure is to provide a microorganism producing O-phosphoserine (OPS).

Another object of the present disclosure is to provide a method of producing OPS comprising culturing the microorganism producing OPS in a medium and recovering OPS from the microorganism or a medium.

Still another object of the present disclosure is to provide a method of producing cysteine or derivatives thereof, comprising:

a) producing O-phosphoserine by culturing the microorganism producing OPS in a medium; and b) reacting OPS produced in the step a) or a medium comprising the same with a sulfide in the presence of O-phosphoserine sulfhydrylase (OPSS) or a microorganism expressing the same.

Advantageous Effects of the Invention

The OPS-producing microorganism of the present disclosure has resistance to OPS of high concentration and is capable of producing OPS with high efficiency, and can thereby be advantageously used in L-cysteine synthesis, etc.

Best Mode

To achieve the above objects, an aspect of the present disclosure provides a microorganism producing O-phosphoserine (OPS).

As used herein, the term "O-phosphoserine" (hereinafter, "OPS") refers to an ester compound of serine and phosphoric acid which is a component for various proteins. In particular, the OPS, as a precursor of L-cysteine, can be converted into cysteine by reacting with a sulfide under the catalysis of OPS sulfhydrylase (OPSS) (Korean Patent No. 1381048).

As used herein, the term "OPS production" refers to producing OPS in a microorganism as well as producing OPS, which is within a microorganism, outside the microorganism, for example, exporting it to a medium.

As used herein, the term "microorganism producing OPS" refers to a prokaryotic or eukaryotic microorganism strain capable of producing OPS in an organism, and specifically to a microorganism capable of accumulating OPS in a medium or within the microorganism itself by way of genetic manipulation or natural mutation. Specifically, in the present disclosure, the OPS-producing microorganism, as a strain having strong resistance to OPS, may comprise *Escherichia coli* deposited under Accession No. KCCM11815P, in which the inhibition of cell growth is low even at a high concentration of OPS, and which also has excellent OPS productivity.

For example, the microorganism may be a microorganism in which the ability of influx of OPS into a cell or degradation of OPS is further reduced.

Besides the content described above with respect to the OPS-producing microorganism, the content disclosed in Korean Patent No. 1381048 or in U.S. Patent Publication No. 2012-0190081 can be used as reference materials for the present disclosure.

Still another object of the present disclosure is to provide a method for producing OPS, comprising: culturing the microorganism producing OPS in a medium and recovering OPS from the cultured microorganism or the cultured medium.

As used herein, the term "culture" refers to growing a microorganism in an appropriately adjusted environment. In the present disclosure, the culture process may be performed using an appropriate medium and culture conditions well known in the art. The culture process may be easily adjusted for use by one of ordinary skill in the art according to the strain being selected. Specifically, the culture may be performed in a batch process, continuous culture, and fed-batch culture, but is not limited thereto.

The carbon sources contained in the medium may include sugars and carbohydrates such as glucose, sucrose, lactose, fructose, maltose, starch, and cellulose; oil and fats such as soybean oil, sunflower oil, castor oil, and coconut oil, and fatty acids such as palmitic acid, stearic acid, and linolenic acid; alcohols such as ethanol; and organic acids such as acetic acid, which may be used alone or as a mixture, but the carbon sources are not limited thereto. The nitrogen sources contained in the medium may include organic nitrogen sources (e.g., peptone, yeast extract, malt extract, gravy, corn steep liquor, and soybean wheat) and inorganic nitrogen sources (e.g., urea, ammonium sulfate, ammonium chloride, ammonium phosphate, ammonium carbonate, and ammonium nitrate) which may be used alone or in combination, but the nitrogen sources are not limited thereto. The phosphorus sources contained in the medium may include potassium dihydrogen phosphate, dipotassium hydrogen phosphate, and corresponding sodium-containing salts, but the phosphorus sources are not limited thereto. In addition, the medium may include metal salts such as magnesium sulfate or iron sulfate, and further, amino acids, vitamins, suitable precursors, etc. may be included. These media or precursors may be added in a batch culture process or continuous culture process to a culture, but are not limited thereto.

During the culture period, the pH of a culture may be adjusted by adding a compound such as ammonium hydroxide, potassium hydroxide, ammonia, phosphoric acid, and sulfuric acid to the culture in an appropriate manner. Additionally, during the culture period, an antifoaming agent, such as fatty acid polyglycol ester, may be added to prevent foam generation. Additionally, to maintain the aerobic state of the culture, oxygen or oxygen-containing gas may be injected into the culture, and to maintain the anaerobic and microaerobic states of the culture, culture may be performed without the injection of gas, or nitrogen, hydrogen, or carbon dioxide gas may be injected. The culture temperature may normally be from 27° C. to 37° C., and specifically from 30° C. to 35° C. The culture may be continued until the production of desired material(s) can be obtained, and specifically for 10 hours to 100 hours, but is not limited thereto.

In the present disclosure, an appropriate condition for growing the microorganism may easily be adjusted for use by one of ordinary skill in the art. For example, although the condition is not limited thereto, glycine or serine may further be added in a medium. Glycine may be provided in the form of purified glycine, yeast extract including glycine, and tryptone, and the concentration contained in the culture medium may normally be 0.1 g/L to 10 g/L, and specifically 0.5 g/L to 3 g/L. In addition, serine may be provided in the form of purified serine, yeast extract containing serine, tryptone, etc., and the concentration contained in the culture medium may normally be 0.1 g/L to 5 g/L, and specifically 0.1 g/L to 1 g/L.

In the present disclosure, OPS produced in the culture process can further be recovered and purified, and the target OPS can be recovered from a culture using an appropriate method known in the art (e.g., a batch-type culture, continuous culture, or fed-batch culture, etc.), but the method is not limited thereto. For example, methods such as centrifugation, filtration, anion exchange chromatography, crystallization, HPLC, etc. may be used, and additionally, the target OPS can be recovered from a medium or a microorganism using appropriate methods known in the art.

Still another aspect of the present disclosure is to provide a method for producing cysteine or a derivative thereof, comprising: a) producing OPS by culturing the OPS-producing microorganism in a medium; and b) reacting OPS produced in step a) or a medium comprising the same with a sulfide in the presence of OPS sulfhydrylase (OPSS) or a microorganism expressing the same.

As used herein, the term "OPS sulfhydrylase (OPSS)" refers to a polypeptide which catalyzes a reaction converting the OPS into cysteine by providing a thiol group (—SH) to OPS. The enzyme was first identified in *Aeropyrum pernix, Mycobacterium tuberculosis, Mycobacterium smegmatis*, and *Trichomonas vaginalis* (Mino K and Ishikawa K, FEB-Sletters, 551: 133-138, 2003; Burns K E et al., J. Am. Chem. Soc., 127: 11602-11603, 2005). Additionally, the OPSS may include wild-type OPSS protein as well as a variant protein which shows an activity equivalent to or greater than the biological activity of wild-type OPSS protein as a sequence wherein part of the sequence of the polynucleotide encoding the OPSS is deleted, substituted, or added. For example, the OPSS protein and variant protein thereof disclosed in Korean Patent Nos. 1381048 and 1208267 may all be included, but are not limited thereto.

The sulfide can be used if the sulfide is any sulfide which is provided in the form of a liquid or gas due to a difference in pH, pressure, and solubility, as well as solids conventionally used in the related technical field which can be converted into the form of a thiol group (—SH group) such as sulfide ($S^{2-}$), thiosulfate ($S_2O_3^{2-}$), etc. Specifically, $Na_2S$, NaSH, $H_2S$, $(NH_4)_2S$, NaSH, and $Na_2S_2O_3$ which provide a thiol group to OPS may be used. As the above reaction is a reaction in which one cysteine or cysteine derivative is prepared by providing one thiol group to one reactive group of OPS, the amount of the sulfide added during the reaction may be 0.1 to 3 times the OPS molar concentration, specifically 1 to 2 times.

In addition, the present disclosure further comprises recovering cysteine or a derivative thereof produced through a reaction of step b). In particular, the desired cysteine or derivative thereof can be separated and purified from the reaction solution using appropriate reactions known in the art.

Additionally, the prepared cysteine above can also be produced as various cysteine derivatives by modifying hydrogen atoms or specific atomic groups of cysteine through chemical synthesis reactions known in the art.

As used herein, the term "derivative" refers to a by-product obtained together in a preparation process of a target compound, and includes a compound similar to a target product, a precursor of a target product, and a similar compound that is obtained by chemically modifying a part of a certain compound. Generally, the derivative refers to a compound in which a hydrogen atom or a specific atomic group in the compound is substituted with another atom or atomic group.

As used herein, the term "cysteine derivative" refers to a compound in which hydrogen atom or a specific atomic group of cysteine is substituted with another atom or atomic group, and includes a precursor thereof. For example, a compound may be in a form in which another atom or atomic group is attached to the nitrogen atom in an amine group (—$NH_2$) or to the sulfur atom in a thiol group (—SH) of cysteine, and examples include N-acetylcysteine (NAC), S-carboxymethylcysteine (SCMC), Boc-Cys(Me)—OH, (R)-S-(2-amino-2-carboxyethyl)-L-homocysteine, (R)-2-amino-3-sulfopropionic acid, D-2-amino-4-(ethylthio)butyric acid, 3-sulfino-L-alanine, Fmoc-Cys(Boc-methyl)—OH, seleno-L-cystine, S-(2-thiazolyl)-L-cysteine, S-(2-thienyl)-L-cysteine, S-(4-tolyl)-L-cysteine, etc., but are not limited thereto. Cysteine can easily be converted to N-acetylcysteine (NAC) by reacting with an acetylation agent and can be converted to S-carboxymethylcysteine (SCMC) by reacting with a haloacetic acid under basic conditions. As the cysteine derivative is mainly used as a pharmaceutical raw material, it can be used as a an antitussive, cough suppressor, therapeutic agent for bronchitis, bronchial asthma, or sore throat, etc.

Still another aspect of the present disclosure relates to a use for producing O-phosphoserine of a KCCM11815P microorganism having resistance to O-phosphoserine (OPS).

With respect to the use, the O-phosphoserine-producing microorganism, KCCM11815P, having resistance to O-phosphoserine is as described above.

As described above, the O-phosphoserine-producing microorganism of the present disclosure has strong resistance to OPS, and inhibition of cell growth is low even at a high concentration of OPS, and further, the microorganism has excellent OPS productivity.

DETAILED DESCRIPTION OF THE INVENTION

Hereinafter, the present disclosure will be described in detail through exemplary embodiments. However, these exemplary embodiments are provided for the purpose of illustration only and are not intended to limit the scope of the present disclosure.

Example 1: Selection of a Mutant Strain by a Method of Artificial Mutation

In order to obtain a mutant strain of a microorganism in which the productivity of O-phosphoserine (OPS) is enhanced, the method below was used to induce a mutation of the microorganism.

Specifically, *Escherichia coli* W3110 wild-type, a parent strain, was seeded in LB liquid medium and incubated for 12 hours at 37° C. Subsequently, 1 mL of the above culture was seeded into 100 mL of liquid medium and cultured for 5 hours and 30 minutes at 37° C., followed by recovery of 50 mL of the culture medium. The recovered culture was washed with 100 mM citric buffer, followed by addition of N-methyl-N'-nitro-N-nitrosoguanidine (NTG) to make a final concentration of 200 mg/L and treatment for 45 minutes, and then the culture was washed with 100 mM phosphate buffer.

Subsequently, in order to obtain an OPS-producing strain, 20 g/L $KH_2PO_4$ and 10 g/L glucose were added to the M9 minimal medium, and these were solidified, followed by plating the strain treated with the NTG. In particular, the mortality rate in the M9 minimal medium was 97%, and after incubation at 37° C. for 12 hours, an OPS-producing mutant strain was obtained.

The mutant strain obtained with the above method was named *Escherichia coli* CA07-0348 and deposited at the Korean Culture Center of Microorganisms (address: Yurim B/D, 45, Hongjenae-2ga-gil, Seodaemun-gu, Seoul 120-861, Republic of Korea) under Accession No. KCCM11815P on Feb. 26, 2016, under the Budapest treaty.

Composition of M9 Minimal Medium $Na_2HPO_4$ 6.78 g/L, $KH_2PO_4$ 3 g/L, $NH_4Cl$ 1 g/L, NaCl 0.5 g/L, glucose 10 g/L, and agarose 15 g/L

Example 2: Investigation of OPS Productivity of OPS-Producing Mutant Strain

The following experiments were performed to confirm the OPS productivity of *Escherichia coli* CA07-90348, a mutant strain obtained from Example 1 above.

In order to enhance the OPS biosynthetic pathway, a pCL-Prmf-serA*(G336V)-(RBS)serC (Korean Patent No. 1381048) vector was transformed into a W3110 wild-type strain and the CA07-0348 strain above with a conventionally used electric pulse method. Each strain was plated on LB solid medium and cultured overnight in a 33° C. incubator. The strain cultured overnight in LB solid was seeded in 25 mL of the below titration medium, and incubated again at 34.5° C. at 200 rpm for 30 hours. After the incubation, the amount of OPS production was measured using high-performance liquid chromatography, and the OPS concentration in the culture medium for each strain tested is shown in Table 1 below.

The composition of the titration medium used in present Example 2 is as follows.

Titration Medium

Glucose 50 g/L, yeast extract 0.3 g/L, glycine 2.5 g/L, $KH_2PO_4$ 6 g/L, $(NH_4)_2SO_4$ 17 g/L, $MgSO_4.7H_2O$ 1 g/L, $FeSO_4.7H_2O$ 5 mg/L, $MnSO_4.4H_2O$ 10 mg/L, and $CaCO_3$ 30 g/L

TABLE 1

| Strain | $OD_{560\,nm}$ | Glucose Consumption (g/L) | O-Phosphoserine (g/L) | Yield (%) |
| --- | --- | --- | --- | --- |
| W3110 | 21.9 | 40 | 0.0 | 0 |
| CA07-0348 | 20.8 | 8.7 | 1.23 | 14 |
| W3110/ pCL-Prmf-serA*(G336V)-(RBS)serC | 25.1 | 45.3 | 0.0 | 0 |
| CA07-0348/ pCL-Prmf-serA*(G336V)-(RBS)serC | 26.6 | 41.4 | 2.3 | 5.6 |

As can be seen in Table 1 above, the wild-type strain, W3110, never produced OPS, while the mutant strain of the present disclosure, CA07-0348, was confirmed to produce OPS at a concentration of 1.23 g/L. Additionally, in the case where the biosynthetic pathway was enhanced by transformation, the wild-type never produced OPS, while the CA07-0348 strain produced OPS at a concentration of 2.3 g/L, and it was confirmed that the amount of OPS increased before the transformation.

Example 3: Investigation of OPS Resistance of OPS-Producing Mutant Strain

In order to confirm the OPS resistance of *Escherichia coli* CA07-0348, the OPS-producing mutant strain obtained from Example 1 above, culture was performed with the following method.

*Escherichia coli* W3110, a parent strain, and the above mutant strain were seeded in a 15 mL disposable tube containing 2 mL of LB medium and incubated with shaking at 37° C. at 200 rpm for 12 hours, and then the seed culture was obtained. After washing the cultured strain once with phosphate-buffered saline, 100 μt of the seed culture was seeded in a 50 mL disposable tube containing 5 mL of screening medium and incubated at 37° C. at 200 rpm for 20 hours.

The composition of the screening medium used in present Example 3 is as follows.

Screening Medium

Glucose 10 g/L, LB 100 g/L, $H_3PO_4$ 1 g/L, OPS 100 g/L, KOH 0.27 M, and NaOH 0.27 M, pH 7.0

After the incubation, optical density (hereinafter referred to as "OD") was measured by a spectrophotometer, and the OD of the culture medium for each strain tested is shown in Table 2 below.

TABLE 2

Comparison of OD of *Escherichia coli* CA07-0348 in screening medium

|  | W3110 | CA07-0348 |
|---|---|---|
| Optical density ($OD_{560\ nm}$) | 0.20 | 0.39 |

As a result, as shown in Table 2 above, *Escherichia coli* W3110, a parent strain, showed a measured OD value of 0.20 when cultured in a medium (screening medium) containing 100 g/L of OPS for 20 hours, while the mutant strain of *Escherichia coli* CA07-0348 according to the present disclosure showed an OD value of 0.39, thereby confirming that the growth rate was about twice as fast.

The results above indicate that the mutant strain of *Escherichia coli* CA07-0348 showed resistance to 100 g/L of OPS, resulting in less inhibition of cell growth. Accordingly, the microorganism of the present disclosure can be advantageously used in the mass production of OPS.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: CJ CHEILJEDANG
CJ CHEILJEDANG CENTER,
330, DONGHO-RO,
JUNG-GU, SEOUL 100-400,
REPUBLIC OF KOREA

RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br> *Escherichia coli* CA07-0348 | Accession number given by the INTERNATIONAL DEPOSITARY AUTHORITY: <br> KCCM11815P |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on February. 26. 2016. (date of the original deposit)¹ |

| IV. INTERNATIONAL DEPOSITARY AUTHORITY | |
|---|---|
| Name: Korean Culture Center of Microorganisms <br><br> Address: Yurim B/D <br> 45, Hongjenae-2ga-gil <br> Seodaemun-gu <br> SEOUL 120-861 <br> Republic of Korea | Signature(s) of person(s) having the power to represent the International Depositary Authority or of authorized official(s): <br><br> Date: February. 26. 2016. |

¹ Where Rule 6.4 (d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                    Sole page

The invention claimed is:

1. A KCCM11815P microorganism producing O-phosphoserine (OPS), wherein the microorganism has resistance to O-phosphoserine.

2. A method for producing O-phosphoserine, comprising:
   culturing the microorganism of claim 1 in a medium; and
   recovering O-phosphoserine from the microorganism or the medium.

3. A method for producing cysteine or a derivative thereof, comprising:
   a) producing O-phosphoserine by culturing the microorganism of claim 1 in a medium; and
   b) reacting the O-phosphoserine produced in step a) or a medium comprising the same with a sulfide in the presence of O-phosphoserine sulfhydrylase (OPSS) or a microorganism expressing OPSS.

4. The method of claim 3, wherein the sulfide is at least one selected from the group consisting of $Na_2S$, NaSH, $(NH_4)_2S$, $H_2S$, and $Na_2S_2O_3$.

* * * * *